United States Patent [19]
Quercia et al.

[11] Patent Number: 4,756,501
[45] Date of Patent: Jul. 12, 1988

[54] HANGER FOR DRAINAGE DEVICE

[75] Inventors: Riccardo Quercia, Bayside, N.Y.; Quinton J. Farrar, Wyckoff; Frederick A. Everett, Jr., Bloomfield, both of N.J.

[73] Assignee: Pfizer Hospital Products Group, Inc., New York, N.Y.

[21] Appl. No.: 916,343

[22] Filed: Oct. 7, 1986

[51] Int. Cl.$^4$ .................................. B42F 13/00
[52] U.S. Cl. .................... 248/340; 24/230.5 R; 248/215; 248/308; 248/359 H; 248/359 I; 403/350; 403/383
[58] Field of Search ............... 248/340, 341, 339, 215, 248/304, 308, 359 H, 359 I, 359 G; 24/230.5 R; 403/24, 209, 350, 383; 211/119; 16/125, 126

[56] References Cited

U.S. PATENT DOCUMENTS

| Re. 29,877 | 1/1979 | Kurtz et al. |
|---|---|---|
| 2,364,968 | 12/1944 | Gore ........................... 403/209 |
| 2,633,321 | 3/1953 | Coulter ........................ 248/215 |
| 2,652,054 | 9/1953 | Bishop ..................... 248/359 H X |
| 3,363,626 | 1/1968 | Bidwell et al. |
| 3,363,627 | 1/1968 | Bidwell et al. |
| 3,559,647 | 2/1971 | Bidwell et al. |
| 3,683,913 | 8/1972 | Kurtz et al. |
| 3,782,497 | 1/1974 | Bidwell et al. |
| 3,851,846 | 12/1974 | Long ........................... 403/350 X |
| 4,258,824 | 3/1981 | Kurtz et al. |
| 4,372,336 | 2/1983 | Cornell et al. |
| 4,425,125 | 1/1984 | Kurtz et al. |
| 4,428,486 | 1/1984 | Collins ......................... 211/119 |
| 4,439,190 | 3/1984 | Protzmann et al. ............ 137/205 X |
| 4,519,796 | 5/1985 | Russo . |
| 4,533,353 | 8/1985 | Akiyama . |
| 4,540,413 | 9/1985 | Russo . |
| 4,544,370 | 10/1985 | Elliott et al. |

FOREIGN PATENT DOCUMENTS

WO84/03838 10/1984 PCT Int'l Appl.
WO86/01091 2/1986 PCT Int'l Appl.
WO86/01114 2/1986 PCT Int'l Appl.

OTHER PUBLICATIONS

"Understanding Chest Drainage Systems-Deknatel Pleur-evac ®", 1985.
"Airpot", Airpot Corp., 1982.

Primary Examiner—J. Franklin Foss
Assistant Examiner—David L. Talbott
Attorney, Agent, or Firm—Pennie & Edmonds

[57] ABSTRACT

Apparatus for supporting a housing from a support including a bracket member formed of at least two opposed walls and having a post member extending between the walls, one of the walls capable of being positioned on the housing; and a hook member having one end rotatably secured about the post member for selective rotational movement from a first storage position to a second hanging position, the other end of the hook member being configured for engagement with the support, the one end of the hook member and the bracket being configured and dimensioned so that the hook member remains locked in the hanging position.

16 Claims, 5 Drawing Sheets

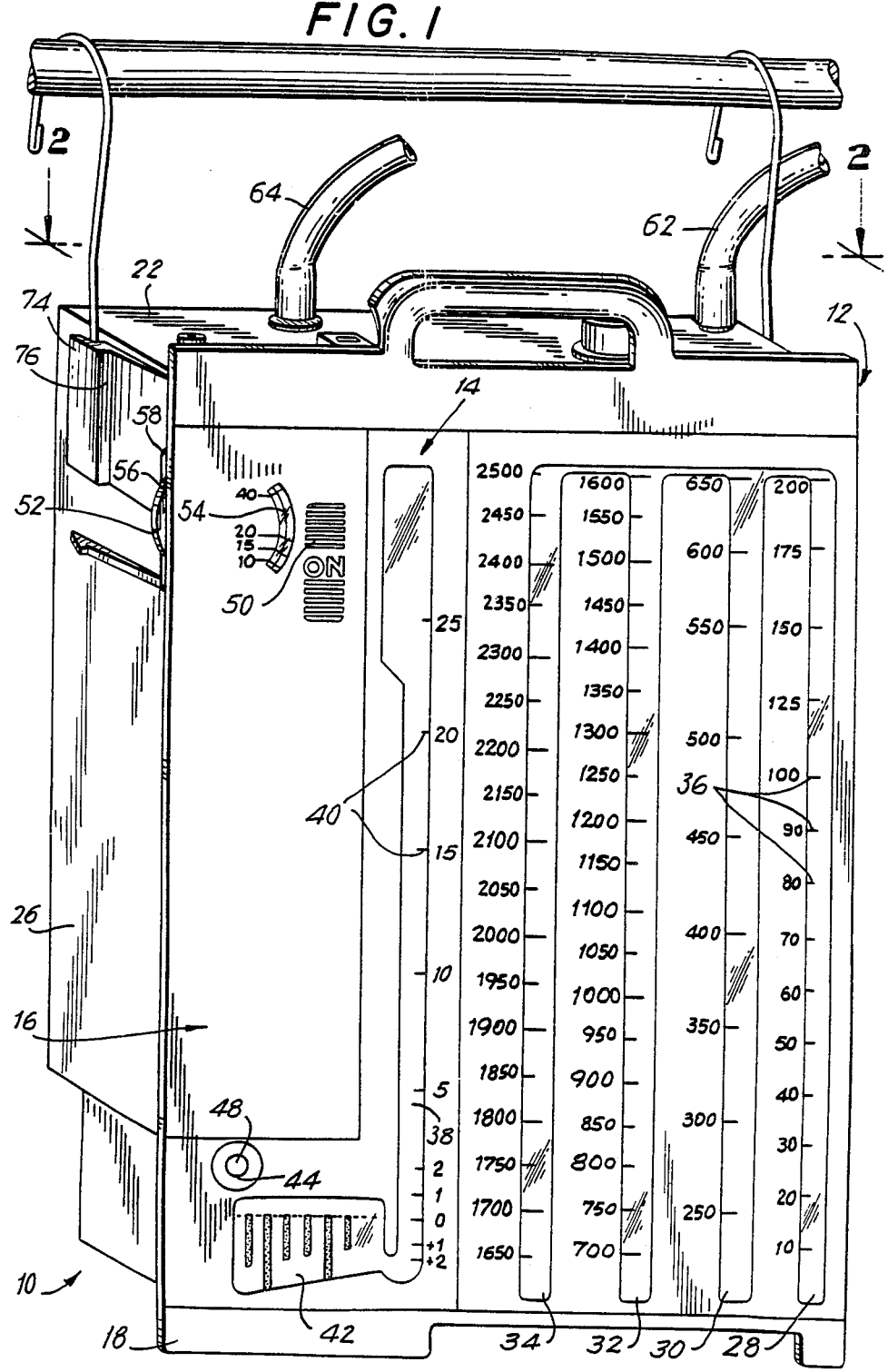

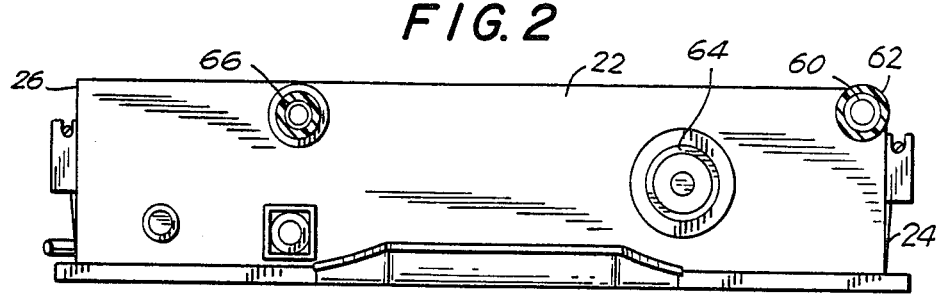
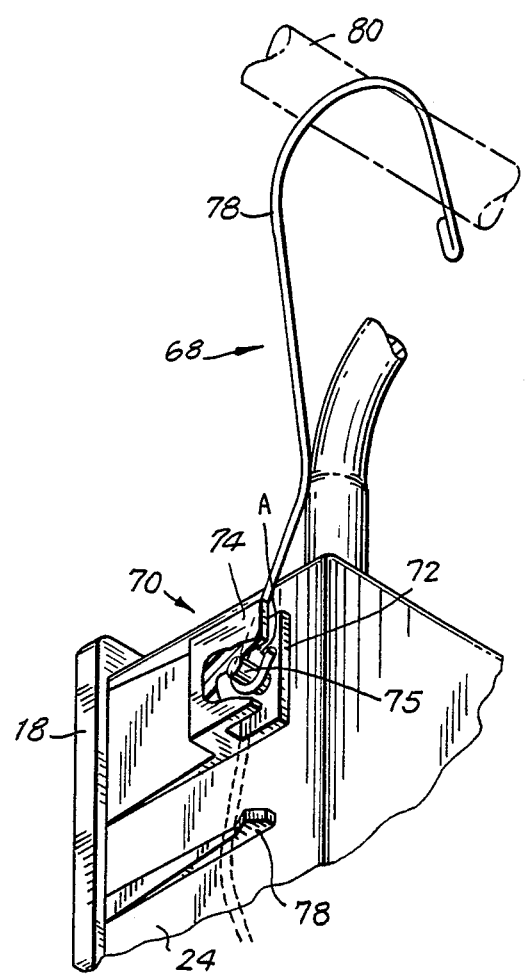

HANGER FOR DRAINAGE DEVICE

TECHNICAL FIELD

The present invention relates to supports for drainage devices and in particular to a hanger for drainage systems which remove gases and fluids from medical patients, such as from the chest cavity, by means of pressure differentials.

BACKGROUND ART

For many years, the standard apparatus for performing the evacuation of the pleural cavity was a drainage system known as the "3-bottle set-up" which includes a collection bottle, a water seal bottle and a suction control bottle. A catheter runs from the patient's pleural cavity to the collection bottle, and the suction bottle is connected by a tube to a suction source. The three bottles are connected in series by various tubes to apply suction to the pleural cavity to withdraw fluid and air and thereafter discharge the same into the collection bottle. Gases entering the collection bottle bubble through water in the water seal bottle. The water in the water seal also usually prevents the back flow of air into the chest cavity.

Suction pressure is usually provided by a central vacuum supply in a hospital so as to permit withdrawal of fluids such as blood, water and gas from a patient's pleural cavity by establishing a pressure differential between the suction source and the internal pressure in the patient. Such suction pressure and pressure differentials must be precisely maintained because of the dangerous conditions which could result if unduly high or low pressure differentials should occur. However, the bottles typically were placed on a support such as a table or floor and could be knocked over and the tubes pulled out accidentally.

The 3-bottle set-up lost favor with the introduction of an underwater seal drainage system sold under the name "Pleur-evac" ® in 1966 by Deknatel Inc.[1] U.S. Pat. Nos. 3,363,626; 3,363,627; 3,559,647; 3,683,913; 3,782,497; 4,258,824; and Re. 29,877 are directed to various aspects of the Pleur-evac ® system which over the years has provided improvements that eliminated various shortcomings of the 3-bottle set-up. These improvements have included the elimination of variations in the 3-bottle set-up that existed between different manufacturers, hospitals, and hospital laboratories, such variations including bottle size, tube length and diameter, stopper material and the like.

[1] A more detailed description of the need for and the proper use of chest drainage devices is presented in the Deknatel Inc. Pleur-evac ® publication entitled "Physiology of the Chest and Thoracic Catheters; Chest Drainage Systems No. 1 of a series from Deknatel" (1985) which is incorporated herein in its entirety.

Among the features of the Pleur-evac ® system which provide its improved performance are employment of 3-bottle techniques in a single, pre-formed, self-contained unit. The desired values of suction are generally established by the levels of water in the suction control bottle and the water seal bottle. These levels are filled according to specified values prior to the application of the system to the patient. A special valve referred to as the "High Negativity Valve" is included which is employed when the patient's negativity becomes sufficient to threaten loss of the water seal. Also, a "Positive Pressure Release Valve" in the large arm of the water seal chamber works to prevent a tension pneumothorax when pressure in the large arm of the water seal exceeds a prescribed value because of suction malfunction, accidental clamping or occlusion of the suction tube. The Pleur-evac ® system is disposable and helps in the battle to control cross-contamination.

The Pleur-evac ® is provided with hanger hooks to permit supporting the device, for example, from a hospital bed. However, the hooks are easily removable from the device and are loosely attached which still permit dislodging the Pleur-evac ® from its support by inadvertent jostling and the like.

Despite the advantages of the Pleur-evac ® system over the 3-bottle set-up and the general acceptance of the device in the medical community, there remains a continuing need to improve the convenience and performance of chest drainage systems and to render such systems compact.

We have invented an improved hanger means for a drainage device which provides additional improvements to presently available devices.

SUMMARY OF THE INVENTION

The present invention is directed to an apparatus for supporting a housing from a support, comprising bracket member formed of at least one wall and having a post member extending therefrom, said post also capable of being positioned on the housing; and hook member having one end rotatably secured about the post member for selective rotational movement from a first storage position to a second hanging position, the other end of the hook member being configured for engagement with the support, the one end of the hook member and the bracket being configured and dimensioned so that the hook member remains locked in the hanging position.

Preferably the one end is curved in a hook-like configuration with the smallest distance of separation of the hooked end being smaller than the diameter of the post member such that when the hook member is selectively rotated to the second hanging position, the hooked end can be moved away from the post member which is then securely advanced toward the smallest distance whereupon the hooked end resiliently spreads apart so as to lock the hook member in the second hanging position. A retention means is also provided which is configured for attachment to the housing so as to securely retain the hook member when in the first storage position. The other end of the hook member is curved so as to be capable of hanging from the support. In a preferred embodiment, a bracket and hook member are disposed on each of two opposite walls of the housing.

In addition, the present invention relates to a drainage device for draining fluids from a portion of a body comprising a housing; collection chamber formed within the housing for collecting fluids including an inlet for entry of the fluids and for fluid communication with the body portion; suction control chamber formed within the housing and being in fluid communication with the collection chamber for regulating the degree of vacuum imposed in the collection chamber; and hanger means disposed on the housing for supporting the housing from a support, the hanger means comprising bracket member formed of at least one wall and having a post member extending therefrom, said post also capable of being positioned on the housing; and hook member having one end rotatably secured about the post member for selective rotational movement from a first storage position to a second hanging position, the other end of the hook member being configured for engagement with the support, the one end of the hook member and the bracket being configured and dimensioned so that the hook member remains locked in the hanging position.

Preferably the housing is formed of a front wall member and a back wall member sealed together along their peripheries by a plurality of side wall members. Also the front wall member includes an integrally formed handle. The suction inlet and collection chamber inlet are each disposed in a first side wall common to the seal chamber and the collection chamber. Moreover, the ambient inlet to the suction control chamber is disposed in a second side wall adjacent to the first side wall.

BRIEF DESCRIPTION OF THE DRAWINGS

The present invention is described in greater detail hereinbelow, with reference to the drawings wherein:

FIG. 1 is a perspective view of a chest drainage device supported in a hanging position with hangers according to the present invention.

FIG. 2 is a top view of the drainage device of FIG. 1 illustrating a pair of hangers of the present invention positioned at the sides of the chest drainage device.

FIG. 3 is an enlarged, partially exposed perspective view of one of the hangers of FIG. 1.

DESCRIPTION OF THE PREFERRED EMBODIMENTS

Figure 4:
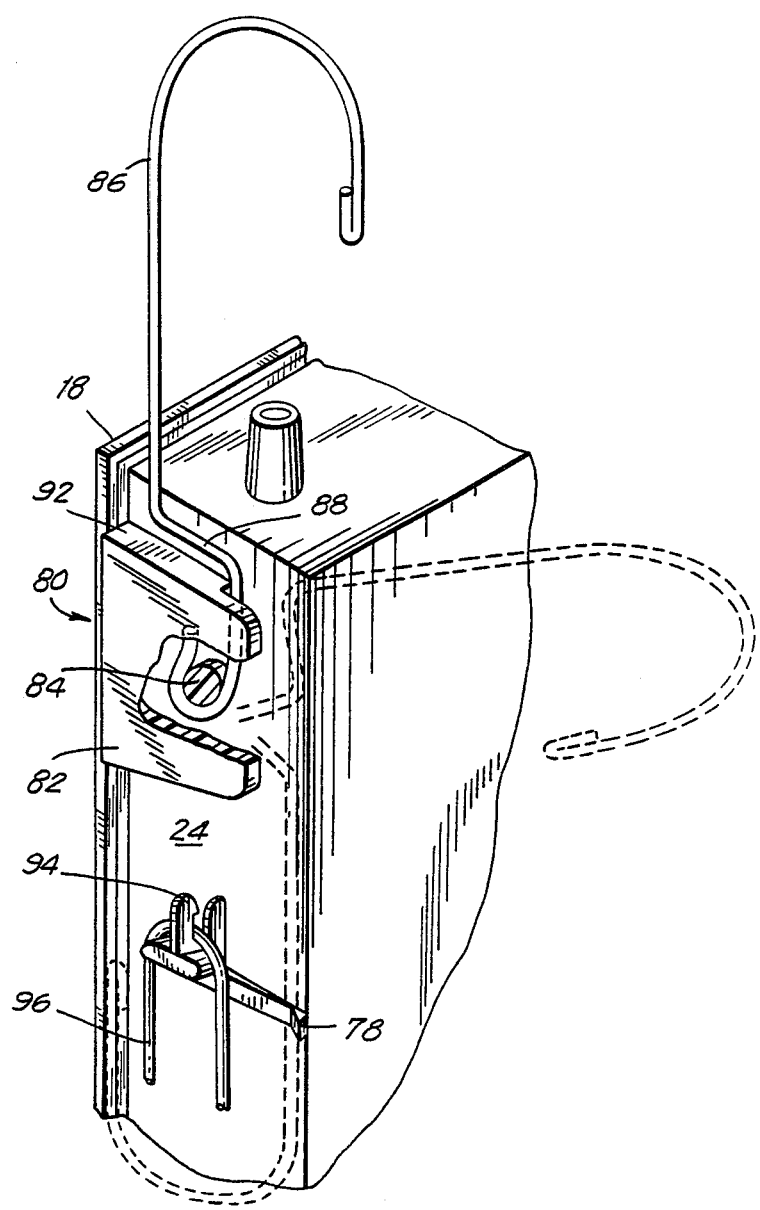
FIG. 4 is an enlarged, partially exposed perspective view of an alternative embodiment of the hangers of the present invention.

In the description which follows, any reference to either orientation or direction is intended primarily for the purpose of illustration and is not intended in any way as a limitation of the scope of the present invention.

Referring to FIG. 1, a chest drainage device 10 is illustrated with three chambers—a collection chamber 12 for retaining and storing fluids collected from a body cavity, a water seal chamber 14 for preventing any fluid from entering into the collection chamber 12 during high levels of negative pressure in the body cavity and a dry suction control chamber 16. The function and operation of these various chambers are generally described in U.S. Pat. Nos. 3,363,626; 3,363,627; 3,559,647; 3,683,913; 3,782,497; 4,258,824; and Re. 29,877 to the extent that like or common elements are presented therein. In addition, the purpose and general operation of the various chambers of the chest drainage device 10 of the present invention are also more fully described in the Deknatel Inc. Pleur-evac ® publication entitled "Understanding Chest Drainage Systems" (1985) which is incorporated herein in its entirety. Accordingly, the disclosure of the aforementioned patents and publication are incorporated herein in their entirety.

As shown in FIG. 1, the drainage device 10 is generally formed of a housing that includes a front wall 18 secured to a back wall 20 as shown in FIG. 2 by means of four side walls which include a top wall 22, right side wall 24, left side wall 26 and bottom wall (not shown). The housing can be formed integrally with all the walls formed along their peripheries or, alternatively the separate side walls and front and back walls can be secured to one another by means well known to those skilled in the art concerning securement or attachment procedures.

In order to permit viewing of the contents of the collection chamber, the front wall 18 as shown in FIG. 1 is at least transparent at certain portions thereof which overlay the heights of the various collection compartments 28, 30, 32, 34. Also, the heights are calibrated with graduations 130 which indicate the amount of fluid collected therein. The smaller volumetric size of the first collection compartment 28 permits finer measurements, for example, from 0–200 cc of fluid while the other compartments accommodate still larger volumetric amounts. In this manner, the medical personnel can readily evaluate the performance of the chest drainage device 10 as the amount of fluid collected over time and during a complete fluid evacuation procedure by a single reading of the height of the fluid in the most recently filled collection compartment.

Other portions of front wall 18 are also transparent to permit the viewing of other operational features of the device 10. In this respect, the small arm compartment 38 of the seal chamber 14 is transparent in order to permit a viewing of the height of the fluid contained within the seal chamber 14. Accordingly, the length of the small arm compartment 38 is also calibrated with gradations 40 in order to permit measurement of the height of the fluid therein. Similarly an airflow meter 48 of the type illustrated and described in U.S. Pat. No. 3,683,913 has a transparent portion 42 which permits viewing of any air bubbles passing therethrough. Grommets 44 and 46 include a central rubber portion 48 which permit injection of fluid by means of a hypodermic needle which will penetrate but not do damage the rubber seal which thereafter seals and retains the integrity of the respective chambers or portions thereof. The suction control chamber 16 includes a compartment 50 which is partially viewable through a respective transparent portion in wall 18.

In order to permit visual determination of the proper level of suction setting desired, a control disk 52 is viewable through transparent portion 54 in wall 18 which indicates readily the degree of suction which is selected by means of movement of lever arm 56 extending through opening 58 of left side wall 26.

An inlet port 60 is positioned in top wall 38 so that fluid and gases from a body cavity pass directly into collection compartment 12 through tubing 62. A high negativity valve 62 is positioned in top wall 22 in communication with collection chamber 12. The high negativity valve includes a button actuated valve which when depressed allows filtered air to enter the collection chamber 12. In this manner, undesired high degrees of negative pressure that may occur in the body cavity and thereby develop in the collection chamber 12 are relieved.

As shown in FIG. 1, the device 10 is coupled to a suction source by means of a suitable tubing 64 that is connected over the suction inlet 66.

As shown in FIG. 3, the hanger device 68 according to the present invention includes a bracket member 70 which is formed of two opposed walls 72 and 74 which have between them a post member 75 extending between walls. As shown in FIG. 3, one of the walls 72 is positioned or attached onto side wall 24 of drainage device 10. As shown more clearly in FIG. 1, the opposed walls 72 and 74 are joined together in common side wall 76 whose function will be more clearly explained hereinbelow. The hanger device 68 also includes a hook member 78 which is formed of a wire that is curved at both ends. At its upper end, the wire 78 has a greater curve so as to accommodate the larger diameter of a bedpost, for example 80. At the lower curved end, the wire 78 is hooked so as to permit the small curved end to be positioned about post member 75. The small curved end has a smallest distance of separation indicated by letter A which is less than the diameter of post member 75. The smaller curved end of wire 78 is resilient so that when the hook member is selectively rotated to the hanging position as shown in FIG. 3, the hooked small curved end can be moved away from post member 75 which is then securely advanced toward the smallest distance separation "A" whereupon the hooked end resiliently spreads apart so as to lock the hook member in the hanging position.

When the hanger member is not needed to support the housing, the wire 78 can be moved so as to pull the post member 75 out of the smallest distance or separation which thereupon resiliently snaps back to its former distance of separation and thus retains the hook member about the post member 75. Thereafter, the hook member can be rotated downwardly and the wire 78 passed over and retained against a retention shoulder 78 positioned below the bracket 70 as shown in FIG. 3. Notably, the hooked end can rotate about post member 75 but is at all times retained thereabout since the common side wall 76 prevents the hooked end from separating from the post member 75. Alternatively, if common side wall 76 is not provided, the front wall 18 extends about the side walls in the manner as shown in FIG. 3 sufficiently so that if the hooked end advances past the post member 75, it will eventually engage the extended post of the front wall 18 and will not be permitted to move any farther. This once again retains the hook member relatively to the bracket member 70.

Figure 4A:
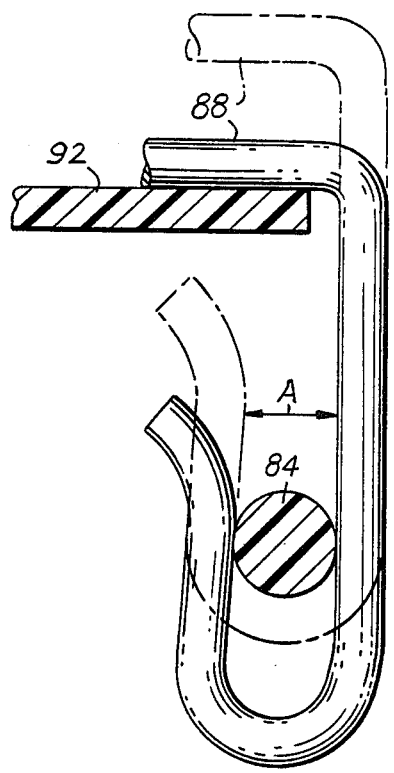
FIG. 4A is an enlarged, partially exposed side view of the hook member of FIG. 4 in a locked or secured position.

Referring to FIG. 4, an alternative embodiment of the hanger device 68 according to the present invention is shown. In this alternative embodiment, a bracket member 80 includes a wall 82 which has extending therefrom a post member 84 that is attached at its other end to the side wall 24 of the housing. The wall 82 extends to the front wall 18 as shown specifically FIG. 4. The hanger device 80 also includes a hook member 86 which is formed of a wire that is curved at both ends as is the case with hook member 78. Similarly, the purposes of the hooked ends of or curved ends of hook member 86 are similar to those described previously in connection with hook member 78. However, the hook member 86 has a portion 88 which is bent so that when the hook member 86 is rotated from a stored position shown by dotted phantom lines 90 up through and to the stored position as shown by the solid lines of hook member 86 in an upright position, the bent portion 88 can rest upon the upper wall portion of wall 92 when the hook member 86 is then pressed downwardly so as to spread apart the curved end of hook member 86 about post as shown in FIG. 4A member 84 in the manner as described before with respect to hook member 78.

Figure 5:
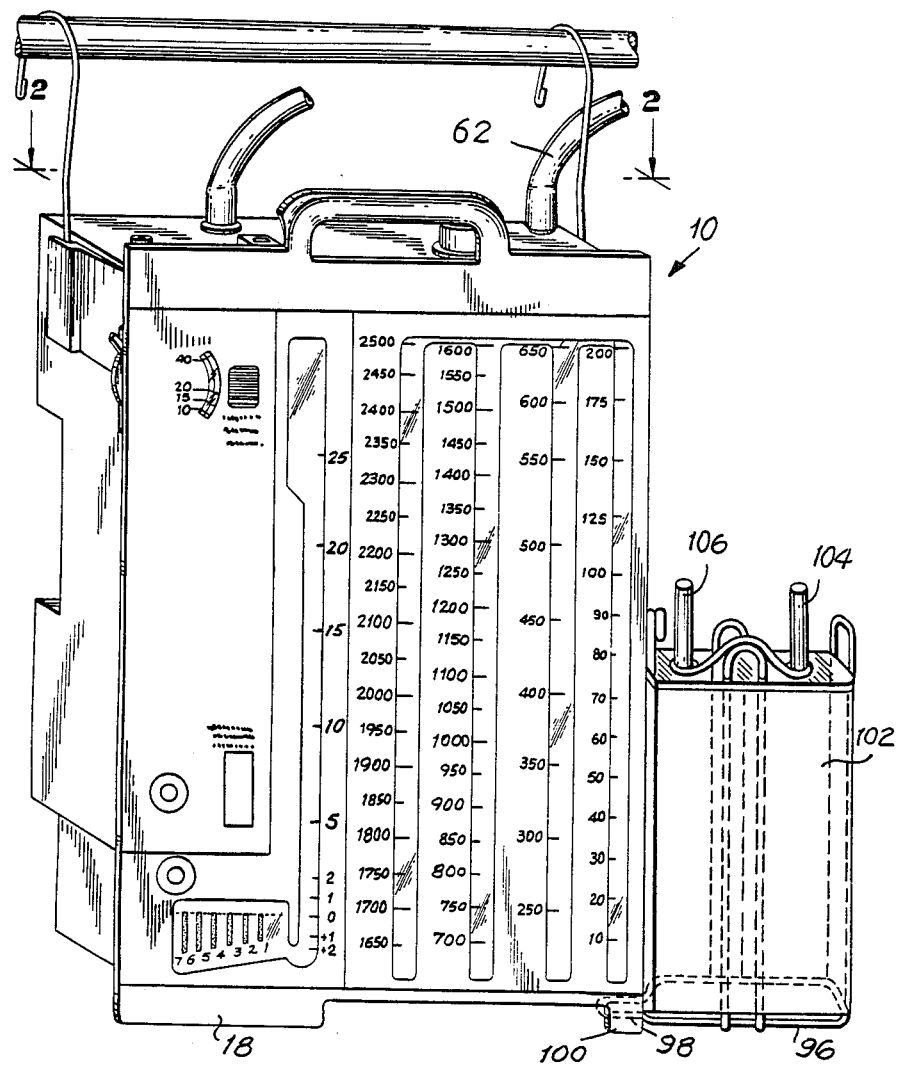
FIG. 5 is a perspective view of a chest drainage device in a hanging position with an autotransfusion device attached to the side thereof.

In the embodiment illustrated in FIG. 4, there is included a hook bracket 94 which receives a wire frame 96 as shown therein. Specifically, the wire frame is as shown generally in FIG. 5 that includes an eye portion 98 that hooks and secures about a lower leg 100 of device or housing or front wall 18. The wire frame 96 supports a bag 102 which is of the type employed in automatic transfusion devices a described and illustrated in U.S. Pat. No. 4,443,220, which is incorporated herein in its entirety. The autotransfusion device includes tube 104 that is connected to the patient's cavity to be drained of fluids and also a tube which is coupled to an inlet 62 of drainage device 10. Notably the automatic transfusion device is incorporated so as to be able to return the fluid collected therein to the patient should the need arise before collecting the same within the drainage device 10.

The present invention has been described in detail with particular emphasis on the preferred embodiments thereof. However, it should be understood that variations and modifications within the spirit and scope of the invention may occur to those skilled in the art to which the invention pertains.

We claim:

1. Apparatus for supporting a housing from a support, comprising:
   a. bracket member formed of at least one wall and having a post member extending therefrom, said post also capable of being positioned on the housing; and
   b. hook member having a first end rotatably secured about said post member for selective rotational movement from a first storage position to a second hanging position, said hook member having a second end being configured for engagement with the support, said first end of said hook member and said bracket being configured and dimensioned so that said hook member upon being rotatably moved to said second hanging position can be selectively displaced relative to said post member so as to remain locked generally in said hanging position, wherein said first end is shaped in a generally hook-like configuration with a smallest distance of separation being smaller than the diameter of the post member such that when said hook member is selectively rotated to said second hanging position, said first end can be selectively displaced relative to said post member by moving away from said post member which is then securely advanced toward said smallest distance whereupon said hooked end resiliently spreads apart so as to lock said hook member about said post member in said second hanging position.

2. The apparatus according to claim 1 wherein said hook member has a bent portion which is configured and dimensioned so as to rest upon said bracket when said first end of said hook member is selectively displaced so that said post member is securely advanced toward said smallest distance of said first end.

3. The apparatus according to claim 1 further comprising a retention means configured for attachment to the housing so as to securely retain the hook member when in said first storage position.

4. The apparatus according to claim 3 wherein said other end of the hook member is curved so as to be capable of hanging from the support.

5. The apparatus according to claim 4 further comprising a bracket and hook member disposed on each of two opposite walls of the housing.

6. Drainage device for draining fluids from a portion of a body comprising:
   a. housing;
   b. collection chamber formed within said housing for collecting fluids including an inlet for entry of the fluids and for fluid communication with the body portion;

c. suction control chamber formed within said housing and being in fluid communication with said collection chamber for regulating the degree of vacuum imposed in the collection chamber; and d. hanger means disposed on said housing for supporting said housing from a support, said hanger means comprising;

1. bracket member formed of at least one wall and having a post member extending therefrom, said post also capable of being positioned on the housing; and 2. hook member having a first end rotatably secured about said post member for selective rotational movement from a first storage position to a second hanging position, said hook member having a second end being configured for engagement with the support, said first end of said hook member and said bracket being configured and dimensioned so that said hook member upon being rotatably moved to said second hanging position can be selectively displaced relative to said post member so as to remain locked in said hanging position, wherein said first end is shaped in a generally hook-like configuration with a smallest distance of separation being smaller than the diameter of the post member such that when said hook member is selectively rotated to said second hanging position, said first end can be selectively displaced relative to said post member by moving away from said post member which is then securely advanced into said smallest distance whereupon said first end resiliently spreads apart so as to lock said hook member about said post member in said second hanging position.

7. The apparatus according to claim 6 wherein said hook member has a bent portion which is configured and dimensioned so as to rest upon said bracket when said first end of said hook member is selectively displaced so that said post member is securely advanced toward said smallest distance of said first end.

8. The apparatus according to claim 6 further comprising a retention means configured for attachment to the housing so as to securely retain the hook member when in said first storage position.

9. The apparatus according to claim 8 wherein said other end of the hook member is curved so as to be capable of hanging from the support.

10. The apparatus according to claim 9 further comprising a bracket and hook member disposed on each of two opposite walls of the housing.

11. The apparatus according to claim 10 wherein said housing is formed of a front wall member and a back wall member sealed together along their peripheries by a plurality of side wall members.

12. The apparatus according to claim 11 wherein said front wall member includes an integrally formed handle.

13. The apparatus according to claim 12 wherein said suction inlet and collection chamber inlet are each disposed in a first side wall common to said seal chamber and said collection chamber 14. The apparatus according to claim 13 wherein said ambient inlet to said suction control chamber is disposed in a second side wall adjacent to said first side wall.

15. The apparatus according to claim 6 further comprising a bracket means disposed on said housing and frame means configured and dimensioned for coupling on said bracket means.

16. The apparatus according to claim 15 further comprising bag means supported by said frame means and being of the type employed in auto-transfusion devices.

* * * * *